United States Patent
Donie et al.

(10) Patent No.: US 6,593,079 B1
(45) Date of Patent: Jul. 15, 2003

(54) METHOD FOR SIMULTANEOUS DETECTION OF HIV ANTIGENS AND HIV ANTIBODIES

(75) Inventors: Frederic Donie, Penzberg (DE); Elke Faatz, Huglfing (DE); Barbara Upmeier, Iffeldorf (DE); Eva Hoess, Munich (DE); Marie-Ange Buyse, Melsen (BE); Eric Saman, Bornem (BE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/381,009

(22) PCT Filed: Mar. 5, 1998

(86) PCT No.: PCT/EP98/01235

§ 371 (c)(1),
(2), (4) Date: Jan. 12, 2000

(87) PCT Pub. No.: WO98/40744

PCT Pub. Date: Sep. 17, 1998

(30) Foreign Application Priority Data

Mar. 10, 1997 (DE) .......................................... 197 09 762
Jul. 1, 1997 (DE) .......................................... 197 27 943

(51) Int. Cl.[7] .............................. C12Q 1/06; C12Q 1/70; G01N 33/53; G01N 33/543; G01N 33/577
(52) U.S. Cl. .............................. 435/5; 435/7.1; 435/7.2; 435/7.7; 435/7.72; 435/7.5; 435/7.8; 435/4; 435/7.91; 435/7.92; 435/7.94; 435/7.95; 436/543; 436/501
(58) Field of Search .......................... 435/4, 5, 7.2, 7.7, 435/7.72, 7.1, 7.91, 7.92, 7.94, 7.95, 971, 7.5, 7.8; 436/543, 501

(56) References Cited

FOREIGN PATENT DOCUMENTS

| DE | 42 36 189 A1 | 4/1994 | .......... G01N/33/53 |
|---|---|---|---|
| EP | 0 186 799 A1 | 7/1986 | |
| EP | 0 265 851 A2 | 5/1988 | |
| EP | 0 280 211 A2 | 8/1988 | |
| EP | 0 386 713 A2 | 9/1990 | |
| EP | 0 595 211 A1 | 5/1994 | |
| WO | WO 93/21346 | 10/1993 | |
| WO | WO-93/21346 | * 10/1993 | |
| WO | WO 96/03423 | 2/1996 | |
| WO | WO 96/03651 | 2/1996 | |
| WO | WO 96/03652 | 2/1996 | |

OTHER PUBLICATIONS

Hashida et al. J. Virol. methods 1996, vol. 62, pp. 43–53.*
Academic Press Dictionary of Science and Technology.*
Clavel, Francois, "Editorial Review HIV–2, the West African AIDS Virus," AIDS 1:135–140 (1987).
Filice, G., et al., "Sensitivity and Specificity of Anti–HIV Elisa Employing Recombinant (p24, p66, gp120) and Synthetic (gp41) Viral Antigenic Peptides," Microbiologica 14:185–194 (1991).
Gitti, Rossitza K., et al., "Structure of the Amino–Terminal Core Domain of the HIV–1 Capsid Protein," Science 273:231–235 (1996).
Hashida, Seiichi, et al., "Earlier Diagnosis of HIV–1 Infection by Simultaneous Detection of p24 Antigen and Antibody IgGs to p17 and Reverse Transcriptase in Serum With Enzyme Immunoassay," Journal of Clinical Laboratory Analysis 10:213–219 (1996).
Muller, Barbara, et al., "Co–expression of the Subunits of the Heterodimer of HIV–1 Reverse Transcriptase in *Escherichia coli*," The Journal of Biological Chemistry 264 (24):13975–13978 (1989).
Saitoh, Atsuchi, et al., "Overproduction of Human Immunodeficiency Virus Type I Reverse Transcriptase in *Escherichia coli* and Purification of the Enzyme," Microbiol. Immunol. 34 (6):509–521 (1990).
Sharp, Paul M., et al., "Origins and diversity of human immunodeficiency viruses," AIDS 8(suppl 1):S27–S42 (1994).

* cited by examiner

Primary Examiner—James Housel
Assistant Examiner—Bao Qun Li
(74) Attorney, Agent, or Firm—Brinks Hofer Gilson & Lione

(57) ABSTRACT

The invention concerns a process for diagnosis of an HIV infection by means of an immunoassay using the specific detection of the p24 antigen of HIV1, HIV1-Sub0 and/or the p26 antigen of HIV2, at least one antibody against the env region of HIV1, HIV1-Sub0 and/or of HIV2 and at least one antibody against the pol and/or gag region of HIV1, HIV1-Sub0 and/or HIV2, reagent kits and test strips suitable for diagnostic procedure as well as monoclonal antibodies against p24 and their use.

12 Claims, 3 Drawing Sheets

```
                        SEQUENCE LISTING

<160> NUMBER OF SEQ ID NOS: 36

<210> SEQ ID NO 1
<211> LENGTH: 25
<212> TYPE: PRT
<213> ORGANISM: Human immunodeficiency virus type 1

<400> SEQUENCE: 1

Asp Lys Gly Asn Ser Ser Gln Val Ser Gln Asn Tyr Pro Ile Val Gln
  1               5                  10                  15

Asn Leu Gln Gly Gln Met Val His Gln
             20                  25

<210> SEQ ID NO 2
<211> LENGTH: 25
<212> TYPE: PRT
<213> ORGANISM: Human immunodeficiency virus type 1

<400> SEQUENCE: 2

Asn Tyr Pro Ile Val Gln Asn Leu Gln Gly Gln Met Val His Gln Ala
  1               5                  10                  15

Ile Ser Pro Arg Thr Leu Asn Ala Trp
             20                  25

<210> SEQ ID NO 3
<211> LENGTH: 25
<212> TYPE: PRT
<213> ORGANISM: Human immunodeficiency virus type 1

<400> SEQUENCE: 3

Gln Met Val His Gln Ala Ile Ser Pro Arg Thr Leu Asn Ala Trp Val
  1               5                  10                  15
```

```
Lys Val Ile Glu Glu Lys Ala Phe Ser
            20                  25

<210> SEQ ID NO 4
<211> LENGTH: 25
<212> TYPE: PRT
<213> ORGANISM: Human immunodeficiency virus type 1

<400> SEQUENCE: 4

Thr Leu Asn Ala Trp Val Lys Val Ile Glu Glu Lys Ala Phe Ser Pro
  1               5                  10                  15

Glu Val Ile Pro Met Phe Ser Ala Leu
            20                  25

<210> SEQ ID NO 5
<211> LENGTH: 25
<212> TYPE: PRT
<213> ORGANISM: Human immunodeficiency virus type 1

<400> SEQUENCE: 5

Glu Lys Ala Phe Ser Pro Glu Val Ile Pro Met Phe Ser Ala Leu Ser
  1               5                  10                  15

Glu Gly Ala Thr Pro Gln Asp Leu Asn
            20                  25

<210> SEQ ID NO 6
<211> LENGTH: 25
<212> TYPE: PRT
<213> ORGANISM: Human immunodeficiency virus type 1

<400> SEQUENCE: 6

Met Phe Ser Ala Leu Ser Glu Gly Ala Thr Pro Gln Asp Leu Asn Thr
  1               5                  10                  15

Met Leu Asn Thr Val Gly Gly His Gln
            20                  25

<210> SEQ ID NO 7
<211> LENGTH: 25
<212> TYPE: PRT
<213> ORGANISM: Human immunodeficiency virus type 1

<400> SEQUENCE: 7

Pro Gln Asp Leu Asn Thr Met Leu Asn Thr Val Gly Gly His Gln Ala
  1               5                  10                  15

Ala Met Gln Met Leu Lys Glu Thr Ile
            20                  25

<210> SEQ ID NO 8
<211> LENGTH: 25
<212> TYPE: PRT
<213> ORGANISM: Human immunodeficiency virus type 1

<400> SEQUENCE: 8

Val Gly Gly His Gln Ala Ala Met Gln Met Leu Lys Glu Thr Ile Asn
  1               5                  10                  15

Glu Glu Ala Ala Glu Trp Asp Arg Val
            20                  25

<210> SEQ ID NO 9
<211> LENGTH: 25
<212> TYPE: PRT
<213> ORGANISM: Human immunodeficiency virus type 1
```

```
<400> SEQUENCE: 9

Leu Lys Glu Thr Ile Asn Glu Glu Ala Ala Glu Trp Asp Arg Val His
 1               5                  10                  15

Pro Val His Ala Gly Pro Ile Ala Pro
            20                  25

<210> SEQ ID NO 10
<211> LENGTH: 25
<212> TYPE: PRT
<213> ORGANISM: Human immunodeficiency virus type 1

<400> SEQUENCE: 10

Glu Trp Asp Arg Val His Pro Val His Ala Gly Pro Ile Ala Pro Gly
 1               5                  10                  15

Gln Met Arg Glu Pro Arg Gly Ser Asp
            20                  25

<210> SEQ ID NO 11
<211> LENGTH: 25
<212> TYPE: PRT
<213> ORGANISM: Human immunodeficiency virus type 1

<400> SEQUENCE: 11

Gly Pro Ile Ala Pro Gly Gln Met Arg Glu Pro Arg Gly Ser Asp Ile
 1               5                  10                  15

Ala Gly Thr Thr Ser Thr Leu Gln Glu
            20                  25

<210> SEQ ID NO 12
<211> LENGTH: 25
<212> TYPE: PRT
<213> ORGANISM: Human immunodeficiency virus type 1

<400> SEQUENCE: 12

Pro Arg Gly Ser Asp Ile Ala Gly Thr Thr Ser Thr Leu Gln Glu Gln
 1               5                  10                  15

Ile Gly Trp Met Thr Asn Asn Pro Pro
            20                  25

<210> SEQ ID NO 13
<211> LENGTH: 25
<212> TYPE: PRT
<213> ORGANISM: Human immunodeficiency virus type 1

<400> SEQUENCE: 13

Ser Thr Leu Gln Glu Gln Ile Gly Trp Met Thr Asn Asn Pro Pro Ile
 1               5                  10                  15

Pro Val Gly Glu Ile Tyr Lys Arg Trp
            20                  25

<210> SEQ ID NO 14
<211> LENGTH: 25
<212> TYPE: PRT
<213> ORGANISM: Human immunodeficiency virus type 1

<400> SEQUENCE: 14

Thr Asn Asn Pro Pro Ile Pro Val Gly Glu Ile Tyr Lys Arg Trp Ile
 1               5                  10                  15

Ile Leu Gly Leu Asn Lys Ile Val Arg
            20                  25
```

```
<210> SEQ ID NO 15
<211> LENGTH: 25
<212> TYPE: PRT
<213> ORGANISM: Human immunodeficiency virus type 1

<400> SEQUENCE: 15

Ile Tyr Lys Arg Trp Ile Ile Leu Gly Leu Asn Lys Ile Val Arg Met
 1               5                  10                  15
Tyr Ser Pro Val Ser Ile Leu Asp Ile
            20                  25

<210> SEQ ID NO 16
<211> LENGTH: 25
<212> TYPE: PRT
<213> ORGANISM: Human immunodeficiency virus type 1

<400> SEQUENCE: 16

Asn Lys Ile Val Arg Met Tyr Ser Pro Val Ser Ile Leu Asp Ile Arg
 1               5                  10                  15
Gln Gly Pro Lys Glu Pro Phe Arg Asp
            20                  25

<210> SEQ ID NO 17
<211> LENGTH: 25
<212> TYPE: PRT
<213> ORGANISM: Human immunodeficiency virus type 1

<400> SEQUENCE: 17

Ser Ile Leu Asp Ile Arg Gln Gly Pro Lys Glu Pro Phe Arg Asp Tyr
 1               5                  10                  15
Val Asp Arg Phe Tyr Lys Thr Leu Arg
            20                  25

<210> SEQ ID NO 18
<211> LENGTH: 25
<212> TYPE: PRT
<213> ORGANISM: Human immunodeficiency virus type 1

<400> SEQUENCE: 18

Glu Pro Phe Arg Asp Tyr Val Asp Arg Phe Tyr Lys Thr Leu Arg Ala
 1               5                  10                  15
Glu Gln Ala Ser Gln Glu Val Lys Asn
            20                  25

<210> SEQ ID NO 19
<211> LENGTH: 25
<212> TYPE: PRT
<213> ORGANISM: Human immunodeficiency virus type 1

<400> SEQUENCE: 19

Tyr Lys Thr Leu Arg Ala Glu Gln Ala Ser Gln Glu Val Lys Asn Trp
 1               5                  10                  15
Met Thr Glu Thr Leu Leu Val Gln Asn
            20                  25

<210> SEQ ID NO 20
<211> LENGTH: 25
<212> TYPE: PRT
<213> ORGANISM: Human immunodeficiency virus type 1

<400> SEQUENCE: 20

Gln Glu Val Lys Asn Trp Met Thr Glu Thr Leu Leu Val Gln Asn Ala
```

Asn Pro Asp Cys Lys Thr Ile Leu Lys
            20                  25

<210> SEQ ID NO 21
<211> LENGTH: 25
<212> TYPE: PRT
<213> ORGANISM: Human immunodeficiency virus type 1

<400> SEQUENCE: 21

Leu Leu Val Gln Asn Ala Asn Pro Asp Cys Lys Thr Ile Leu Lys Ala
 1               5                  10                  15

Leu Gly Pro Ala Ala Thr Leu Glu Glu
            20                  25

<210> SEQ ID NO 22
<211> LENGTH: 25
<212> TYPE: PRT
<213> ORGANISM: Human immunodeficiency virus type 1

<400> SEQUENCE: 22

Lys Thr Ile Leu Lys Ala Leu Gly Pro Ala Ala Thr Leu Glu Glu Met
 1               5                  10                  15

Met Thr Ala Cys Gln Gly Val Gly Gly
            20                  25

<210> SEQ ID NO 23
<211> LENGTH: 25
<212> TYPE: PRT
<213> ORGANISM: Human immunodeficiency virus type 1

<400> SEQUENCE: 23

Ala Thr Leu Glu Glu Met Met Thr Ala Cys Gln Gly Val Gly Gly Pro
 1               5                  10                  15

Gly His Lys Ala Arg Val Leu Ala Glu
            20                  25

<210> SEQ ID NO 24
<211> LENGTH: 25
<212> TYPE: PRT
<213> ORGANISM: Human immunodeficiency virus type 1

<400> SEQUENCE: 24

Gln Gly Val Gly Gly Pro Gly His Lys Ala Arg Val Leu Ala Glu Ala
 1               5                  10                  15

Met Ser Gln Val Thr Asn Ser Ala Thr
            20                  25

<210> SEQ ID NO 25
<211> LENGTH: 25
<212> TYPE: PRT
<213> ORGANISM: Human immunodeficiency virus type 1

<400> SEQUENCE: 25

Arg Val Leu Ala Glu Ala Met Ser Gln Val Thr Asn Ser Ala Thr Ile
 1               5                  10                  15

Met Met Gln Arg Gly Asn Phe Arg Asn
            20                  25

<210> SEQ ID NO 26
<211> LENGTH: 25
<212> TYPE: PRT

<213> ORGANISM: Human immunodeficiency virus type 1

<400> SEQUENCE: 26

Thr Asn Ser Ala Thr Ile Met Met Gln Arg Gly Asn Phe Arg Asn Gln
 1               5                  10                  15

Lys Lys Thr Val Lys Cys Phe Asn Cys
            20                  25

<210> SEQ ID NO 27
<211> LENGTH: 25
<212> TYPE: PRT
<213> ORGANISM: Human immunodeficiency virus type 1

<400> SEQUENCE: 27

Gly Asn Phe Arg Asn Gln Lys Lys Thr Val Lys Cys Phe Asn Cys Gly
 1               5                  10                  15

Lys Glu Gly His Ile Ala Lys Asn Cys
            20                  25

<210> SEQ ID NO 28
<211> LENGTH: 25
<212> TYPE: PRT
<213> ORGANISM: Human immunodeficiency virus type 1

<400> SEQUENCE: 28

Lys Cys Phe Asn Cys Gly Lys Glu Gly His Ile Ala Lys Asn Cys Arg
 1               5                  10                  15

Ala Pro Arg Leu Lys Gly Cys Trp Lys
            20                  25

<210> SEQ ID NO 29
<211> LENGTH: 25
<212> TYPE: PRT
<213> ORGANISM: Human immunodeficiency virus type 1

<400> SEQUENCE: 29

Ile Ala Lys Asn Cys Arg Ala Pro Arg Leu Lys Gly Cys Trp Lys Cys
 1               5                  10                  15

Gly Lys Glu Gly His Gln Met Lys Asp
            20                  25

<210> SEQ ID NO 30
<211> LENGTH: 27
<212> TYPE: PRT
<213> ORGANISM: Human immunodeficiency virus type 1

<400> SEQUENCE: 30

Lys Gly Cys Trp Lys Cys Gly Lys Glu Gly His Gln Met Lys Asp Cys
 1               5                  10                  15

Thr Glu Arg Gln Ala Asn Phe Leu Gly Lys Ile
            20                  25

<210> SEQ ID NO 31
<211> LENGTH: 15
<212> TYPE: PRT
<213> ORGANISM: Human immunodeficiency virus type 1

<400> SEQUENCE: 31

Gln Ala Ile Ser Pro Arg Thr Leu Asn Ala Trp Val Lys Val Ile
 1               5                  10                  15

<210> SEQ ID NO 32

```
<211> LENGTH: 11
<212> TYPE: PRT
<213> ORGANISM: Human immunodeficiency virus type 1

<400> SEQUENCE: 32

Ile Ser Pro Arg Thr Leu Asn Ala Trp Val Lys
 1               5                  10

<210> SEQ ID NO 33
<211> LENGTH: 15
<212> TYPE: PRT
<213> ORGANISM: Human immunodeficiency virus type 1

<400> SEQUENCE: 33

Ile Asn Glu Glu Ala Ala Glu Trp Asp Arg Val His Pro Val His
 1               5                  10                  15

<210> SEQ ID NO 34
<211> LENGTH: 11
<212> TYPE: PRT
<213> ORGANISM: Human immunodeficiency virus type 1

<400> SEQUENCE: 34

Glu Glu Ala Ala Glu Trp Asp Arg Val His Pro
 1               5                  10

<210> SEQ ID NO 35
<211> LENGTH: 15
<212> TYPE: PRT
<213> ORGANISM: Human immunodeficiency virus type 1

<400> SEQUENCE: 35

Ile Arg Gln Gly Pro Lys Glu Pro Phe Arg Asp Tyr Val Asp Arg
 1               5                  10                  15

<210> SEQ ID NO 36
<211> LENGTH: 11
<212> TYPE: PRT
<213> ORGANISM: Human immunodeficiency virus type 1

<400> SEQUENCE: 36

Gln Gly Pro Lys Glu Pro Phe Arg Asp Tyr Val
 1               5                  10
```

METHOD FOR SIMULTANEOUS DETECTION OF HIV ANTIGENS AND HIV ANTIBODIES

Figure 1:
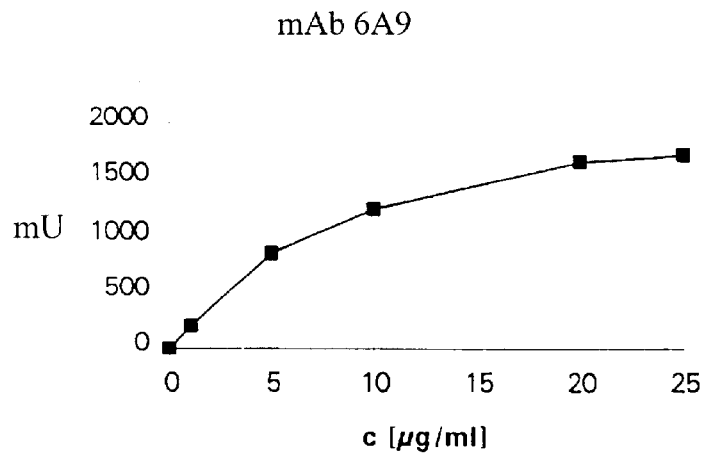

The invention concerns a procedure for diagnosis of an HIV infection by means of an immunoassay using the specific detection of HIV antigens and HIV antibodies.

AIDS (acquired immmunodeficiency syndrome) is an acquired immunodeficiency disease caused by the HIV virus. Hitherto known pathogens are the strains HIV1 and HIV2. Both strains are similar in morphology, cell tropism, interaction with the CD4 receptor of T-cells, their in vitro cytopathic effect on CD4 cells, their general genomic structure and the capability of causing the disease AIDS (Clavel, 1987, AIDS 1, 135–140). The immunological degree of relationship is, however, only small so that generally HIV1 specific antibodies do not show any cross reactions with HIV2. Besides the most common HIV1 group M subtypes a further HIV1 subtype, the subtype 0, is known (Myers et al, Los Alamos data bank, 1994; Sharp et al. AIDS Suppl. 8, pp. 27–42, 1994). The degree of relationship between HIV1-Sub0 and HIV1 is considerably higher than that between HIV1-Sub0 and HIV2. Antibodies directed against HIV1 do, however, only partly cross react with the corresponding antigen of HIV1-Sub0. A large part of the HIV1-Sub0 specific antibodies does not react with the HIV1 group M antigens neither.

The course of an HIV infection can be divided into several diagnostically relevant phases. In the early phase of an infection HIV antigens can already be detected which does not apply to HIV antibodies. In the seroconversion phase HIV antigens can be slightly positive or negative, i.e. not detectable. HIV antibodies of the IgM class are detectable in this phase whereas HIV antibodies of the IgG class are not detectable or only slightly positive. In the next phase, which is without symptoms, mainly HIV antibodies of the IgG type are detectable whereas the HIV antigen does generally not occur. The same is true for the progressive course of disease in the clinical phase.

In the late phase of disease HIV antibodies can finally become slightly positive or negative whereas the HIV antigens remain either negative or can again be detected as positive due to the increase in viral charge with the breakdown of the patient's immune system. Thus, during these different phases of disease which can be—depending on the patient—very different in course there are always moments where antigen or antibody detections may give falsely negative results.

For the detection of HIV1, HIV2 or HIV1-Sub0 infections antibody tests (IgG and IgM) are frequently performed in the bridge test format which is for example described in EP-A-0 280 211. The antigens used are in general antigens of the so-called envelope region (env) which are gp160, gp120, gp41 for HIV1/HIV1-Sub0 and gp140, gp110, gp36 for HIV2, together with the antigen p24 (HIV1) which forms the viral nucleus and p26 (HIV2), respectively. The antigens p24 and p26 are coded by the so-called gag region. These tests give a positive signal if antibodies against the antigens mentioned are present. In the early and late phase of the disease, i.e. when free p24 or p26 antigens are present often no antibodies are detectable since either the patient's immune system has not raised enough antibodies yet or is so exhausted that the number of antibodies built is not sufficient for being detected.

Antigen tests for the detection of p24 antigens and other antibody tests are generally performed separately. The antigen titer of the patient is only increased in the early phase of infection and in the final phase of AIDS so that p24 is only reliably detectable in these phases.

A disadvantage of the hitherto known tests is that none of the tests can cover the total diagnostically relevant period of an HIV infection alone.

With combination tests antigens of a certain pathogen and antibodies directed against this pathogen can be detected simultaneously. Such a procedure for simultaneous determination of antigens and antibodies are disclosed in DE 42 36 189 A1. An approach to diagnostically cover all phases of an HIV infection completely is, however, not described.

In WO 93/21346 a combination test for the simultaneous detection of HIV p24 antigen, HIV1 gp41 antibodies and HIV2 gp36 antibodies (in both cases antibodies against proteins of the env gene) by means of a heterogeneous immunoassay is described. With this test HIV positive samples which do not contain p24 or antibodies against env proteins are, however, not detected as positive. Solely with gp41 not all antibody positive HIV1 samples can be detected since samples characterized by showing an incomplete band pattern in the western blotting and no dyeing of the gp41 band are widespread.

Hashida et al (1996, J. Clin. Lab. Anal. 10, 213–219) describe a diagnostic test for the detection of HIV1 infections. With this test the p24 antigen, IgG antibodies against p17 (from the gag region) and IgG antibodies against reverse transcriptase (RT) coded by the pol gene can be detected. This procedure allows, however, only the detection of HIV1 infections and seroconversion sera containing only low-affine IgM antibodies against the two antigens used above are not detected. Seroconversion sera containing antibodies against env proteins are not detected either. After the decrease in HIV antigen titer in the early phase of infection often only IgM antibodies against the env protein gp41 occur. In this case the Hashida et al. test shows a falsely negative result.

There is no state-of-the-art diagnostic test system which reliably enables the simultaneous detection of HIV1, HIV1-Sub0 and HIV2 completely for all infection stages.

The object of the present invention was therefore to develop an improved test for HIV infections that allows as a single test an accurate, reliable and complete detection of all diagnostically detectable phases of an HIV infection. The test should also allow the simultaneous determination of HIV1, HIV1-Sub0 and HIV2.

This object is achieved by the procedure according to the invention for diagnosis of an HIV infection by means of an immunoassay using the specific detection of p24 antigen of HIV1, HIV1-Sub0 and/or p26 antigen of HIV2, at least one antibody against the env region of HIV1, HIV1-Sub0 and/or HIV2 and at least one antibody against the pol and/or gag region from HIV1, HIV1-Sub0 and/or HIV2. With the procedure according to the invention it is possible to reliably detect an HIV infection already with the occurrence of only one of the analytes mentioned above.

Surprisingly, it has been shown that by the detection of antibodies against a gene product in particular of the pol region of HIV combined with the detection of p24 antigen of HIV1, HIV1-Sub0 and/or p26 antigen of HIV2 and the detection of at least one antibody against the HIV-env region the hitherto deplorable diagnostic gap can be closed. Surprisingly, a procedure for the detection of an HIV infection, where antibodies against the reverse transcriptase (RT) of HIV are detected, combined with the detection of p24 antigen of HIV1, HIV1-Sub0 and/or p26 antigen of HIV2 and the detection of at least one antibody against the HIV-env region has been proven to be particularly suitable.

The detection of an HIV infection by the combination test according to the invention by means of the determination of the single parameters mentioned is performed simultaneously. The term combination test means that HIV antigens and antibodies directed against HIV antigens can be detected simultaneously. With this test all HIV infection stages can be covered reliably. By the selection according to the invention of antigens or antibodies and their corresponding receptors binding specifically it is possible to perform the procedure according to the invention.

Furthermore, the detection of HIV1, HIV1-Sub0 and HIV2 can be achieved using one single test. In addition, by adequately selecting the receptors a broad detection of HIV1 subtypes of the HIV1 group M is possible. The test is preferably based on the principle of heterogeneous immunoassays. Homogeneous procedures such as turbidimetric tests with no separation of the liquid and solid phase are, however, also conceivable.

The receptors R1 and R2 used in the detection procedure according to the invention are receptors that specifically bind to the HIV1-p24 and/or HIV2-p26 antigen to be determined. The receptors used as R3 and R4 receptors are one or several antigens of the env region of HIV1, HIV2 or HIV1-Sub0 (gp160, gp120, gp41 for HIV1/HIV1-Sub0 and gp140, gp110, gp36 for HIV2). The receptors used preferably as R3 and R4 are gp41 and/or gp36 or fragments thereof. The receptors used as R5 and R6 are one or several antigens from the pol or gag region of HIV1, HIV2, or HIV1-Sub0, but should not be epitopes or sequences of p24 or p26 possibly reacting with the receptors R1 or R2. Antigens of the pol region of HIV1, HIV2 or HIV1-Sub0 are preferably used as R5 and R6. The reverse transcriptase (RT) is used particularly preferably as receptor R5 and R6.

The combination of receptors according to the invention allows to reliably detect all stages of an HIV infection. This allows the detection of HIV specific analytes which are only present in the early or late phase of infection (e.g. p24 and p26 antigen, respectively) as well as of analytes occurring in the asymptomatic phase and detectable over a longer period of time, like e.g. antibodies directed against the env gene products gp160, gp120 or gp41 and antibodies against the pol gene products reverse transcriptase, integrase or protease or antibodies against the gag gene products p17 or p15.

By adequately selecting the receptors infections with HIV1, HIV2 and HIV1-Sub0 including all HIV1 subtypes of the M group can, optionally be detected. For such a procedure the receptors selected as R1 and R2 specifically bind to the p24 antigen of HIV1. In this case the selection of R1 and R2 should enable the recognition and binding of HIV1-p24 and HIV1-Sub0-p24. This may require the use of several receptors for R1 and R2 so that all HIV1 group M subtypes and the HIV1 subtype0 are detected. In addition, for the simultaneous detection of HIV1, HIV2 and HIV1-Sub0 either the corresponding cross-reacting receptors or further receptors R1 and R2 are used which also specifically recognize the p26 antigen of HIV2. The total number of receptors R1 and R2 to be used depends on the cross reactivity or homology of the epitopes selected. In the case of a good selection it is possible to reduce the number of receptors used. Receptors specifically binding to antibodies directed against env gene products of HIV1 and HIV1-Sub0 can be used as R3 and R4 receptors. The gp41 antigen (HIV1 and HIV1-Sub0, respectively) or fragments or epitopes thereof are particularly suitable. Further receptors used as R3 and R4 are receptors specifically recognizing antibodies directed against env gene products of HIV2. The gp36 antigen or fragments or epitopes thereof are particularly suitable. Receptors specifically recognizing antibodies against gag or pol gene products of HIV1 and HIV1-Sub0— with the exception of the epitopes of p24 which may react with the receptors R1 and R2—are suitable as R5 and R6 receptors. For the recognition of HIV2 further R5 and R6 receptors specifically binding to antibodies against gag or pol gene products of HIV2 can be used additionally. The receptors preferred for R5 and R6 are receptors recognizing antibodies against the pol gene products of HIV1 and HIV1-Sub0, and of HIV2, respectively. Among the receptors R5 and R6 against the three possible pol gene products reverse transcriptase, integrase and protease the receptors recognizing antibodies against the reverse transcriptase are particularly preferred.

A further subject matter of the invention is the above mentioned procedure for the detection of an HIV infection with the receptors R1 and R2 used each as a single receptor or in the form of mixtures of various receptors. If mixtures are used the receptors preferably recognize different epitopes of p24 and p26, respectively. The use of receptor mixtures is intended to ensure the recognition of different HIV subtypes—in the case of the p24 antigen the recognition of HIV1 group M subtypes and HIV1-Sub0—using one single test composition.

According to the invention the detection procedure is also suitable for infections with the HIV1 subtype 0.

Furthermore, the detection procedure according to the invention can also be used for infections with the HIV1 subtypes of the M group.

According to the invention the receptors R3, R4, R5 and R6 can also each be used in the form of mixtures of different receptors to ensure that HIV1-, HIV1-Sub0- and HIV2-positive samples are reliably recognized in one test preparation. It must, however, always be ensured that the different receptors do not considerably disturb each other when binding to the antigen to be detected or the antibody to be detected. The receptors preferred as R3 and R4 are those presenting each the same epitopes. This ensures that the antigen binding parts of the antibody to be detected link both receptors R3 and R4. Depending on the demands combinations of different epitopes can be used too. Recombinant gp41 could for instance be used as R3 and peptides derived from gp41 or polyhaptens—as described in WO96/03652— could be used as R4. This also applies to the receptors R5 and R6. Depending on the demands combinations of different epitopes can be used. Receptors with the same epitopes are, however, preferred.

The procedure according to the invention is generally applied as a wet test. Besides the so-called wet tests with test reagents in a liquid phase all usual dry test formats suitable for the detection of proteins or antibodies can be used too. These dry tests or test strips as for instance described in EP-A-0 186 799 combine all test components on one single carrier.

The procedure according to the invention, preferably performed as a heterogeneous immunoassay, follows the sandwich principle when detecting the antigens with the receptors R1 and R2. The antigen to be detected (here: p24 and p26, respectively) is bound on both sides like a sandwich by R1 and R2. The binding of the antibodies by the receptors R3, R4, R5 and R6 follows the bridge test principle. The antibody to be detected bridges the receptors R3 and R4. The same applies to the receptors R5 and R6. Both test procedures, the sandwich and the bridge test, can be performed simultaneously within the same preparation without disturbing each other. It is therefore also possible to incubate all receptors with the sample and to perform the procedure in a few steps. A washing step for isolation of unbound receptors and sample components before the detection reaction is advantageous, but not indispensable. The receptors R1, R3 and R5, which are suitable for binding to the solid phase can be bound in the liquid phase or can already be bound to the solid phase. The total incubation of all receptors R1 to R6 is preferred. The solid phase to which R1, R3 and R5 may bind can already be present or can be added later or later reached by diffusion or transfer.

During incubation the sandwich is formed between the solid phase R1.p24(p26).R2, the bridge between the solid phase.R3.HIV anti-env antibody.R4 and the bridge between solid phase.R5.HIV-anti-gag/pol antibody.R6. Subsequently, the solid phase is separated from the liquid phase in the case of a heterogeneous immunoassay, the solid phase is washed if necessary and the label of R2, R4 and R6 is determined. The label is for the most part measured at the solid phase but can also be determined in the liquid phase.

If one or several of the receptors R1, R3 and R5 are already bound to the solid phase the sample and the corresponding receptors, i.e. R2, R4 and R6 are added to the solid-phase bound receptors R1, R3 and R5 and incubated together. It is also possible to bring the sample first together with the receptors R1, R3 and R5 in the presence or absence of the solid phase and to add the receptors R2, R4 and R6 in the next step.

A further subject matter of the invention is a procedure for the detection of antibodies against HIV by means of an immunoassay wherein the receptors R3, R4, R5 and R6 are used. The receptors R1 and R2 are not used in this pure antibody test. The receptors used as R3 and R4 are one ore several antigens of the env range of HIV1, HIV2 or HIV1-Sub0 (gp160, gp120, gp41 for HIV1/HIV1-Sub0 and gp140, gp110, gp36 for HIV2) as previously described in the combination test. Gp41 and/or gp36 or fragments thereof are preferably used as receptors R3 and R4. The receptors used as R5 and R6 are—as previously described in the combination test—one or several antigens from the pol or gag region of HIV1, HIV2 or HIV1-Sub0. The receptors used as R5 and R6 are preferably from the pol region of HIV1, HIV2 or HIV1-Sub0. The reverse transcriptase (RT) is particularly preferable for the use as receptor R5 and R6.

The procedure of the antibody detection, the test formats as well as the properties of the receptors used are analogous to those of the combination test so that they are not mentioned separately here. The details concerning the receptors R1 and R2 given in the following apply to the combination test of HIV antibodies and HIV antigens described above. The details concerning the receptors R3, R4, R5 and R6 apply to the combination test as well as to the procedure for the detection of HIV antibodies.

An essential component of receptor R1 is an antibody specifically binding to the p24 antigen of HIV1 and, optionally of HIV1-Sub0 or the p26 antigen of HIV2. Antibodies of all subclasses suitable for specifically binding to p24 or p26 can be used. Instead of complete antibodies fragments such as Fab-, Fab'- or F(ab')$_2$ fragments can of course be used, too.

The antibodies can be polyclonal provided they do not show any cross reactivity to the remaining test components. But since the demands made on the specificity of the anti-p24 and anti-p26 antibodies must be great with regard to the HIV subtype recognition monoclonal antibodies are preferably used. Therefore, the subject matter of the invention also concerns monoclonal antibodies against the p24 antigen. The properties of these antibodies are described in more detail in one of the following paragraphs.

R1 can either be bound directly to the solid phase or the binding to the solid phase is indirect via a specific binding system. The direct binding of R1 to the solid phase follows methods known to the expert. If the binding is performed indirectly via a specific binding system R1 is a conjugate consisting of an antibody against p24 or p26 and a reaction partner of a specific binding system. A specific binding system consists in this case of two reaction partners able of reacting specifically with each other. Their binding capacity can be based on an immunological reaction or a different specific reaction. The specific binding system preferably used is a combination of biotin and avidin or biotin and streptavidin. Further combinations preferred are biotin and antibiotin, hapten and anti-hapten, Fc fragment of an antibody and antibodies against this Fc fragment or carbohydrate and lectin. One of the reaction partners of this pair suitable for specifically binding is, consequently, part of the conjugate forming the R1 receptor.

The other reaction partner of the specific binding system for R1 is the coating of the solid phase. The binding of the other reaction partner of the specific binding system to an insoluble carrier material can be performed according to the usual methods known to the expert. In this case a covalent as well as an adsorptive binding is appropriate. Test tubes or micro-titer plates made of polystyrene or similar plastics which are coated at the inner surface with a reactant of the specific binding system are suitable for use as solid phase. Other suitable substances preferred in particular are particle-size substances like for example latex particles, magnetic particles, molecular sieve materials, glass bodies, plastic tubes, etc.

Porous, lamellar carriers like paper can be used as a carrier, too. Particularly preferred are magnetic beads coated in turn with the corresponding binding partner of the specific binding system described above. For the detection reaction these microparticles can be separated from the liquid phase, e.g. by filtration, centrifugation or, in the case of magnetic particles by a magnet after completing the test reaction.

The R2 receptor consists of one antibody binding specifically to the p24 antigen of HIV1 and, optionally of HIV1-Sub0, respectively or to the p26 antigen of HIV2 and a label. As in the case of the R1 receptor antibodies of all subclasses suitable for specifically binding to p24 or p26 can be used. Instead of complete antibodies their fragments such as Fab-, Fab'- or F(ab')$_2$ fragments can of course be used, too. The antibodies can be polyclonal or monoclonal. As in the case of R1 monoclonal antibodies are used preferably. The monoclonal antibodies according to the invention against the p24 antigen as described in one of the following paragraphs are particularly preferred for R2 too. It is important that the antibodies used in R1 and R2 recognize at least 2 different epitopes of the p24 and p26 antigen, respectively. Both receptors R1 and R2 must be suitable for binding specifically and simultaneously to p24 and p26 to form the sandwich. The epitopes recognized by the antibody components in R1 and R2 must therefore be separated in space. This means that the epitopes recognized by R1 and R2 may overlap but it must be ensured that both receptors can bind simultaneously to the p24 or p26 antigen. The condition that both receptors do not considerably disturb each other when binding to p24 or p26 has to be always fulfilled.

When selecting receptor mixtures for R1 and R2 it is also possible to use the same receptors for R1 and R2. A certain number of R1 receptors would then be suitable for binding to the solid phase and the remaining R1 receptors would not be suitable for binding to the solid phase and would carry the label instead. The same is valid for R2 too. The sandwich can be formed with the orientation solid phase.R1.p24.R2 and solid phase.R1 (R2 epitope).p24.R2 (R1-epitope).

A further component of the R2 receptor is the label. As a label a directly detectable substance, e.g. a chemiluminescent, electrochemiluminescent, fluorescent or radioactive substance or a metal-sol, latex or gold particle is used. Enzymes or other molecules like haptens (e.g. digoxigenin) or fluorescent stain, e.g. fluorescein are also preferred as a label. A particularly preferred label are electrochemiluminescent metal chelates as described in WO 96/03651. Ruthenium complexes are preferably used as metal chelates and also disclosed in WO 96/03651. The methods of labeling are known to the expert and need no further explanation here. The label is detected—as generally known—by measuring the chemiluminescent, fluorescent or radioactive substance or the metal-sol, latex or gold particle or by measuring the substrate transformed by the enzyme.

The label can also be detected indirectly by a further receptor, which is in turn coupled to a signal producing group, binding specifically to the label of R2, e.g. a hapten like digoxigenin. The production of hapten labeled and in particular digoxigenin labeled receptors is described in WO 96/03423.

The detection of the signal producing group, e.g. an electrochemiluminescent, fluorescent or radioactive substance or an enzyme or gold particle, is performed according to methods known to the expert. An antibody or an antibody fragment binding specifically to the label of R2 can for example be used as a further receptor. If this indirect label detection is applied the label of R2 is preferably digoxigenin or a different hapten; the detection is carried out with an antibody directed against digoxigenin or the hapten and labeled with peroxidase or a different label as described above.

As components of the receptors R1 and R2 monoclonal antibodies or their fragments are preferably used. The subject matter of the present invention therefore also concerns monoclonal antibodies binding specifically and with sufficient affinity to the p24 antigen of HIV1 to form a sandwich. Monoclonal antibodies can be used in all tests known to the expert for the detection of a protein like for example in the sandwich test.

The monoclonal antibodies according to the invention can belong to a multitude of immunoglobulin classes (Ig). The monoclonal antibodies preferably belong to the IgG1 class. The coupling of further components like for example labels such as enzymes or haptens or binding partners necessary for the binding of the antibody to a solid phase in heterogeneous immunoassays can preferably be performed with IgG1 antibodies. The production of antibody fragments like e.g. F(ab')$_2$, Fab' or Fab fragments is not problematic with the IgG1 class.

According to the invention the term "monoclonal antibodies" means the complete antibody and fragments thereof usually applied in immunotests and other procedures, e.g. F(ab')$_2$, Fab' or Fab fragments. It also comprises those antibodies produced by modification of the monoclonal antibodies as long as the antigen binding properties were not decisively affected. By measures of genetic engineering, for example parts of the monoclonal antibodies normally produced in mice can be substituted by adequate human antibody sequences to minimize unspecific bindings in immunoassays. Procedures for the production of such chimera monoclonal antibodies are known to the expert for example from Antibody Engineering, J. Mc Cafferty, H. R. Hoogenboom and D. J. Chiswell, The Practical Approach Series, Series Editor: B. D. Hames, Oxford University Press, 1996.

For the suitability of the antibodies the epitopes of p24 which are recognized by the antibodies are essential since they are essential for the recognition of all subtypes. For the p24 epitopes the structure information from Gitti et al (Science 1996, Vol 273, p. 231–235) is used as a basis. Differently produced antibodies recognizing the same epitopes—or epitopes overlapping these epitopes—as the antibodies described in the following are therefore also according to the invention. Such epitopes can for instance be characterized by the Pepscan method. Example 4 of the present application describes the exact procedure of the epitope mapping of the antibodies according to the invention. The epitope region of p24 to which the antibodies according to the invention bind is preferably selected from the group of the following amino acid sequences. These sequences are also listed in the sequence protocol, cf. SEQ ID NO 1–36.

| Sequence | Peptide | SEQ ID NO |
|---|---|---|
| DKGNSSQVSQNYPIVQNLQGQMVHQ | 1 | 1 |
| NYPIVQNLQGQMVHQAISPRTLNAW | 2 | 2 |
| QMVHQAISPRTLNAWVKVIEEKAFS | 3 | 3 |
| TLNAWVKVIEEKAFSPEVIPMFSAL | 4 | 4 |
| EKAFSPEVIPMFSALSEGATPQDLN | 5 | 5 |
| MFSALSEGATPQDLNTMLNTVGGHQ | 6 | 6 |
| PQDLNTMLNTVGGHQAAMQMLKETI | 7 | 7 |
| VGGHQAAMQMLKETINEEAAEWDRV | 8 | 8 |
| LKETINEEAAEWDRVHPVHAGPIAP | 9 | 9 |
| EWDRVHPVHAGPIAPGQMREPRGSD | 10 | 10 |
| GPIAPGQMREPRGSDIAGTTSTLQE | 11 | 11 |
| PRGSDIAGTTSTLQEQIGWMTNNPP | 12 | 12 |
| STLQEQIGWMTNNPPIPVGEIYKRW | 13 | 13 |
| TNNPPIPVGEIYKRWIILGLNKIVR | 14 | 14 |
| IYKRWIILGLNKIVRMYSPVSILDI | 15 | 15 |
| NKIVRMYSPVSILDIRQGPKEPFRD | 16 | 16 |
| SILDIRQGPKEPFRDYVDRFYKTLR | 17 | 17 |
| EPFRDYVDRFYKTLRAEQASQEVKN | 18 | 18 |
| YKTLRAEQASQEVKNWMTETLLVQN | 19 | 19 |
| QEVKNWMTETLLVQNANPDCKTILK | 20 | 20 |
| LLVQNANPDCKTILKALGPAATLEE | 21 | 21 |
| KTILKALGPAATLEEMMTACQGVGG | 22 | 22 |
| ATLEEMMTACQGVGGPGHKARVLAE | 23 | 23 |
| QGVGGPGHKARVLAEAMSQVTNSAT | 24 | 24 |
| RVLAEAMSQVTNSATIMMQRGNFRN | 25 | 25 |
| TNSATIMMQRGNFRNQKKTVKCFNC | 26 | 26 |
| GNFRNQKKTVKCFNCGKEGHIAKNC | 27 | 27 |
| KCFNCGKEGHIAKNCRAPRLKGCWK | 28 | 28 |
| IAKNCRAPRLKGCWKCGKEGHQMKD | 29 | 29 |
| KGCWKCGKEGHQMKDCTERQANFLGKI | 30 | 30 |
| QAISPRTLNAWVKVI | 3A | 31 |
| ISPRTLNAWVK | 3B | 32 |
| INEEAAEWDRVHPVH | 9A | 33 |
| EEAAEWDRVHP | 9B | 34 |
| IRQGPKEPFRDYVDR | 17A | 35 |
| QGPKEPFRDYV | 17B | 36 |

The subject matter of the invention concerns monoclonal antibodies against HIV1 p24 antigen which specifically bind to the p24 epitopes according to SEQ ID NO: 1–36.

A further subject matter of the invention are monoclonal antibodies against the HIV1 p24 antigen which specifically bind to the p24 epitopes according to SEQ ID NO: 3, 9, 17, 31 or 34. These sequences are indicated in bold characters in the list above.

The p24 epitopes according to SEQ ID NO: 3, 9,17, 31 or 34 represent a further subject matter of the invention.

The monoclonal antibodies according to the invention can for example be produced from the cell lines mAb<p24>M-6A9/5, mAb<p24>M-4B1/1, mAb<p24>M-6D9/4, or mAb<p24>M-2E7/3. The cell lines mAb<p24>M-4B1/1 (deposit number DSM ACC2299), mAb<p24>M-6D9/4 (deposit number DSM ACC2300) and mAb<p24>M-

2E7/3 (deposit number DSM ACC2301) were deposited at the German collection of microorganisms and cell cultures ("Deutsche Sammiung von Mikroorganismen und Zellkulturen (DSMZ) GmbH, Mascheroder Weg 1b, D-38124 Braunschweig) on 26.02.97. The cell line mAb<p24>M-6A9/5 was deposited as DSM ACC2310 (deposit number) at the DSMZ on 11.06.97.

The epitope mapping procedure described in example 4 showed that the antibodies produced from the cell line mAb<p24>M-6A9/5 do not recognize a sequential epitope but bind to a conformation epitope of p24.

The same procedure showed that the antibodies produced from the cell line mAb<p24>M-2E7/3 (DSM ACC2301) bind to the epitope corresponding to a peptide according to SEQ ID NO:9 (p24 structure information according to Gitti et al 1996, Science 273, 231–235). It could also be shown that the actual epitope concerned is even smaller. For the specific binding of the mAb<p24>M-2E7/3 to p24 an epitope according to SEQ ID NO: 34 comprising only 11 amino acids is sufficient.

The same procedure showed that the antibodies produced from the cell line mAb<p24>M-6D9/4 (DSM ACC2300) bind to the epitope corresponding to a peptide according to SEQ ID NO: 3. It has also been shown that the epitope necessary for the specific binding is even smaller: for the specific binding of the mAb<p24>M-6D9/4 to p24 an epitope according to SEQ ID NO: 31 comprising 15 amino acids is sufficient.

The same procedure showed that the antibodies produced from the cell line mAb<p24>M-4B1/1 (DSM ACC2299) bind to the epitope corresponding to an epitope according to SEQ ID NO: 17.

The antibodies produced from the cell lines mAb<p24>M-4B1/1 and mAb<p24>M-6D9/4 do not only bind to the p24 epitopes of HIV1 previously characterized but also of HIV1-Sub0. For the simultaneous recognition of the p24 antigen of HIV1 and HIV1-subtype0 the antibodies produced from these cell lines are particularly suitable. Example 5 depicts the testing of the antibodies according to the invention with regard to the p24 subtype recognition. Out of the two antibodies mAb<p24>M-4B1/1 is used preferably on the solid phase side, i.e. as receptor R1 and mAb<p24>M-6D9/4 is used preferably as receptor R2.

For an efficient simultaneous recognition of HIV1 and HIV1-Sub0 the antibodies mAb<p24>4B1/1 and mAb<p24>6A9 are used preferably as R1 and mAb<p24>2E7/3 an mAb<p24>6D9/4 as R2 since this combination ensures the most comprehensive recognition of different HIV1 and HIV1-subtype0 virus isolates (see example 5).

A further subject matter of the invention are antibodies, preferably monoclonal antibodies, binding in an equivalent way to p24 like the monoclonal antibodies mAb<p24>M-6A9/5 (DSM ACC2310), mAb<p24>M-4B1/1 (DSM ACC2299), mAb<p24>M-6D9/4 (DSM ACC2300) or mAb<p24>M-2E7/3 (DSM ACC2301). To "bind in an equivalent way" means here that these antibodies bind to p24 with the same affinity or with a comparably high affinity as the monoclonal antibodies deposited. This can for example be detected when performing appropriate tests with BIAcore® or with the 2-step-sandwich ELISA according to example 4.

A further subject matter of the invention are antibodies , preferably monoclonal antibodies, binding in an equivalent way to p24 like the deposited antibodies mAb<p24>M-6A9/5 (DSM ACC2310), mAb<p24>M-4B1/1 (DSM ACC2299), mAb<p24>M-6D9/4 (DSM ACC2300) or mAb<p24>M-2E7/3 (DSM ACC2301). This can for example be detected by the determination of cross reactivity of the antibodies, e.g. by ELISA competition experiments or tests with BIAcore®. Preferably, these antibodies have a high affinity to p24.

A further subject matter of the invention is the use of at least one of the antibodies described in the above paragraphs in a diagnostic test for the detection of an HIV infection. A further subject matter of the invention is the use of the aforementioned antibodies in the combination test according to the invention for the detection of an HIV infection which is described above too.

The monoclonal antibodies according to the invention can be produced—as already known—by immunization with isolated p24 (isolated from human tissue or recombinant) in suitable test animals like e.g. mice, rats, rabbits and subsequent fusion of the spleen cells of the immunized animals with myeloma cells. Besides spleen cells as lymphocyte source peripheral blood lymphocytes (PBL) or cells of the lymphatic glands from immunized animals (preferably mouse or rat) can be used. For immunization synthetic peptides derived from p24 which can be used alone or coupled to a carrier can be used instead of isolated p24 for the production of the antibodies desired.

Alternatively, lymphocytes from human donors with antibodies developed against p24 can be immortalized. Such lymphocytes producing anti-p24 antibodies can be immortalized either by fusion with a human myeloma cell line or by Epstein-Barr-virus (EBV) transformation to antibody-producing hybridoma cells (Monoclonal Antibody and Immunosensor Technology, A. M. Campbell, Elsevier Verlag 1991; Monoklonale Antikörper, J. H. Peters, H. Baumgarten, Springer Verlag 1990; Monoclonal Antibody Production Techniques and Applications, ed. Lawrence B.Schook, Marcel Dekker Verlag 1987).

An essential component of the R3 receptor is an antigen suitable for specifically binding to the antibodies to be detected and directed against an antigen from the HIV1 or HIV1-Sub0 and/or HIV2-env region. The antigen is preferably suitable for binding to antibodies directed against gp41 or pg120 (HIV1) and gp36 or gp110 (HIV2), particularly preferably suitable for binding to antibodies directed against gp41 and gp36 respectively. The term "antigen" is a molecule capable of specifically binding to an antibody directed against an HIV-env-gene product. The antigen concerned can correspond to the natural antigen. It can therefore be produced in a way isolated from the virus or recombinantly. Synthetic or recombinantly produced peptides suitable for specifically binding to the antibodies to be detected can be used too. The antigen can also be derivatized by other ligands like, e.g. lipids or sugars. Amino acid exchanges (D and L amino acids or allied molecules) or deletions or insertions of amino acids are also possible. Further antigen modifications advantageous for the test procedure, like e.g. the production of polyhaptens described in WO 96/03652 can easily be found out by the expert. The only condition is that inspite of the modifications the antibodies to be determined are still suitable for specifically binding to the modified antigen. This means that the binding site for the antibody/ies on the antigen belonging to R3 must be preserved.

R3 can be bound directly to the solid phase or the binding to the solid phase is indirect via a specific binding system. The direct and indirect binding of R3 to the solid phase is analogous to that of the receptor R1 as described above.

The receptor R4 consists of an antigen suitable for binding specifically to the antibody directed against an antigen from the HIV1 or HIV1-Sub0 and/or HIV2-env region, and a label. The antigen is preferably suitable for binding to an antibody directed against gp41 or gp120 and gp36 or gp110 and particularly preferably suitable for binding to an antibody directed against gp41 and gp36 respectively. The antigen conditions as well as the antigen definition are identical to those mentioned for the R3 receptor. Preferably, the same antigens are used as "antigen components" of the receptors R3 and R4. It is, however, also possible to use different antigens. But it must be ensured that both antigen components of R3 and R4 are suitable for binding to the same antibody to be determined. One condition is that the antibody to be determined always bridges the two receptors R3 an R4.

A further component of the receptor R4 is the label. The conditions of the R4 label are identical to those of the R2 label described above. Preferably, the same labels are used for R2 and R4.

Receptor R5 consists mainly of an antigen suitable for specifically binding to the antibody to be determined directed against an antigen of the pol or gag region of HIV1, HIV1-Sub0 and/or HIV2 which must however not be epitopes or sequences of p24 or p26 possibly reacting with the receptors R1 or R2. The antigen is preferably suitable for binding to an antibody directed against gene products of the pol region and particularly preferably to an antibody directed against the reverse transcriptase (RT). The natural reverse transcriptase (RT) which is a heterodimer (consisting of the two subunits of 51 and 66 kDa) with a relatively native structure is especially appropriate. But the subunits can also be used separately. A recombinantly produced purified RT expressed by an expression clone as for example described at Müller et al. in J. Biol. Chem. 264/24: 13975–13978 (1989) is used particularly preferably. Due to the high degree of amino acid homology between HIV1 and HIV2-RT of about 60% and partly even a 100% correspondence of the two proteins there is generally enough HIV1-RT to be recognized by HIV2 antibodies too. HIV2-RT can, optionally be used alone or additionally. Instead of RT an antigen can be used which is suitable for binding to an antibody directed against gene products of the gag region with the exception of the epitopes of p24 or p26 reacting with the receptors R1 or R2. The antigen is preferably suitable for binding to an antibody directed against gag-p17. The definition of the term "antigen" given for the receptors R3 and R4 also applies to R5 except the specificity: In the case of the receptor R5 the antigen is certainly a molecule suitable for specifically binding to an antibody directed against an HIV-gag or pol gene product.

R5 can be bound directly to the solid phase or the binding is indirect via a specific binding system. The direct and indirect binding of R5 to the solid phase is analogous to that of the receptors R1 and R3 described above.

Receptor R6 consists mainly of an antigen suitable for specifically binding to the antibody to be determined directed against an antigen of the pol or gag region of HIV1, HIV1-Sub0 and/or HIV2. The antigen is preferably suitable for binding to an antibody directed against gene products of the pol region and particularly preferably to an antibody directed against the reverse transcriptase (RT). The details about the antigen properties given above for R5 also apply to R6. The definition of the term "antigen" given for the receptor R5 also applies to R6. Preferably, the same antigens are used as "antigen components" of the receptors R5 and R6. It is, however, also possible to use different antigens. But it must be ensured that both antigen components of R5 and R6 are suitable for binding to the same antibody to be determined. There is always the condition that the antibody to be determined links the two receptors R5 an R6.

A further component of the receptor R6 is the label. The conditions of the R6 label are similar to those of the label of the receptors R2 and R4 described above. Preferably, the same labels are used for R2, R4 and R6.

All antigens used as receptors R3, R4, R5 or R6 can be used separately or, preferably, as cross-linked oligomers or polyhaptens (carrier molecules or particles loaded with the antigens) according to WO 96/03652. This improves the IgM recognition.

All biological liquids known to the expert can be used as samples. The samples preferred are body liquids like whole blood, blood sera, blood plasma, urine, saliva, etc.

Besides the sample, solid phase and the receptors mentioned the test preparations may contain—depending on the use—further additives such as buffers, salts, detergents, protein additives like for example RSA and protein fragments like, e.g. peptone. The additives required are known to the expert or can be found out easily by him.

A further subject matter of the invention is a reagent kit for the detection of an HIV infection, containing at least one receptor R1 suitable for specifically binding to the p24 antigen of HIV1, HIV1-Sub0 and/or the p26 antigen of HIV2, and bound to a solid phase or suitable for binding to it, at least one receptor R2 suitable for specifically binding to the p24 antigen of HIV1, HIV1-Sub0 and/or the p26 antigen of HIV2 and carrying a label, where the epitopes recognized by R1 and R2 are different, at least one receptor R3 suitable for binding to the HIV1, HIV1-Sub0 and/or HIV2 antibody to be determined directed against an antigen from the env region and bound to a solid phase or suitable for binding to it, at least one receptor R4 suitable for specifically binding to the HIV1, HIV1-Sub0 and/or HIV2 antibody to be determined directed against an antigen from the env region and carrying a label, at least one receptor R5 suitable for specifically binding to the HIV1, HIV1-Sub0 and/or HIV2 antibody to be determined directed against an antigen from the pol or gag region and bound to a solid phase or suitable for binding to it, at least one receptor R6 suitable for specifically binding to the HIV1, HIV1-Sub0 and/or HIV2 antibody to be determined directed against an antigen from the pol or gag region and carrying a label as well as other usual additives if necessary.

A further subject matter of the invention is a reagent kit described above wherein the antibodies produced from the cell lines mAb<p24>M-6A9/5, mAb<p24>M-4B1/1, mAb<p24>M-6D9/4 and/or mAb<p24>M-2E7/3 are used as receptors R1 and R2.

Additionally, a subject matter of the invention is a reagent kit for the detection of antibodies against HIV described above and containing the receptors R3, R4, R5 and R6 as well as further usual additives if necessary. The receptors R1 and R2 are not included.

A further subject matter of the invention is a test strip for the detection of an HIV infection carrying at least one receptor R1 suitable for specifically binding to the p24 antigen of HIV1, HIV1-Sub0 and/or the p26 antigen of HIV2, and bound to a solid phase or suitable for binding to it, at least one receptor R2 suitable for specifically binding to the p24 antigen of HIV1, HIV1-Sub0 and/or the p26 antigen of HIV2 and carrying a label, where the epitopes recognized by R1 and R2 are different, at least one receptor R3 suitable for specifically to the HIV1, HIV1-Sub0 and/or HIV2 antibody to be determined directed against an antigen from the env region and bound to a solid phase or suitable for binding to it, at least one receptor R4 suitable for specifically binding to the HIV1, HIV1-Sub0 and/or HIV2 antibody to be determined directed against an antigen from the env region and carrying a label, at least one receptor R5 suitable for specifically binding to the HIV1, HIV1-Sub0 and/or HIV2 antibody to be determined directed against an antigen from the pol or gag region and bound to a solid phase or suitable for binding to it, at least one receptor R6 suitable for specifically binding to the HIV1, HIV1-Sub0 and/or HIV2 antibody to be determined directed against an antigen from the pol or gag region and carrying a label as well as other usual additives if necessary.

A further subject matter of the invention is a test strip for the detection of antibodies against HIV containing the receptors R3, R4, R5 and R6 as well as further usual additives is required. The receptors R1 and R2 are not included.

The FIGS. 1 to 5 depict the following:

FIG. 1: Plateau determination of the monoclonal antibody mAb<p24>M-6A9/5: The determination of the optimum mAb test concentration for epitope mapping is performed according to the procedure described in example 4.2.

Figure 2:
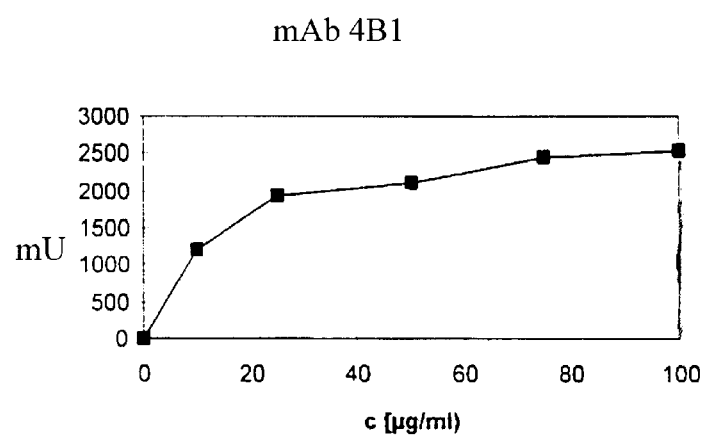

FIG. 2: Plateau determination of the monoclonal antibody mAb<p24>M-4B1/1.

Figure 3:
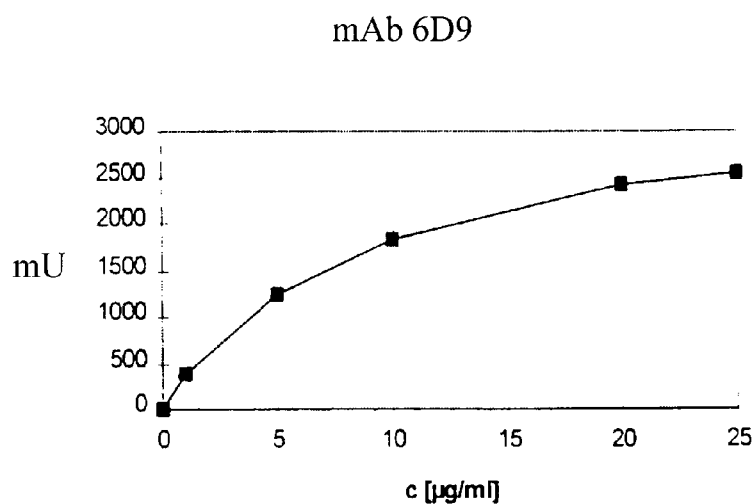

FIG. 3: Plateau determination of the monoclonal antibody mAb<p24>M-6D9/4.

Figure 4:
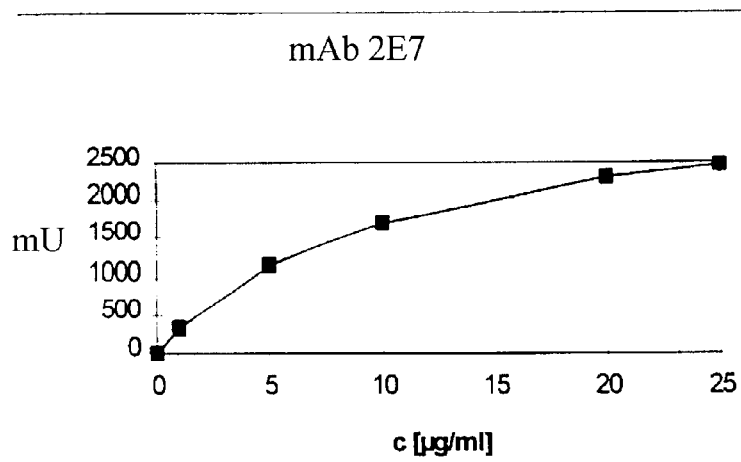

FIG. 4: Plateau determination of the monoclonal antibody mAb<p24>M-2E7/3.

Figure 5:
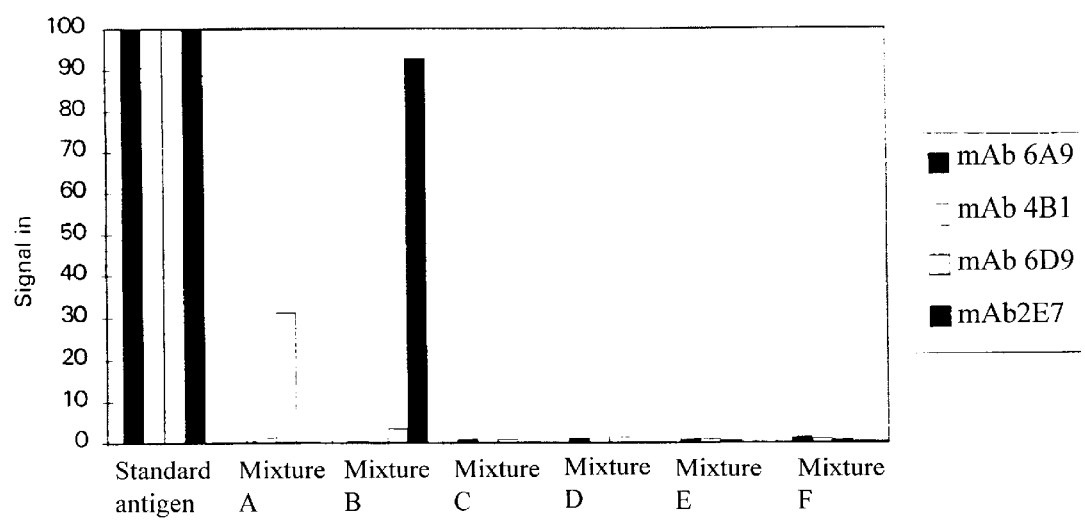

FIG. 5: p24 epitope mapping; reaction of the <p24> monoclonal antibodies with several peptide mixtures according to example 4.2.3.

The invention is further described in the following examples:

EXAMPLES

Example 1

Performance of the Combination Test

The test is performed analogously to the procedure described in the instructions for use of the Enzymun test® anti-HIV1+2+Subtype0 (ref. no. 1557319, Boehringer Mannheim GmbH, Germany). Except the receptors R1 to R6 the reagents and buffers of the Enzymun test® anti-HIV1+2+Subtype0 from the Boehringer Mannheim company GmbH are used. The test is performed at 25° C. on the instrument ES700 (manufacturer: Boehringer Mannheim GmbH, Germany) in a sample volume of 100 μl in streptavidin-coated test tubes according to the principle of the 2-step-sandwich ELISA. The following reagents are used:

Incubation buffer: Tris 25 mM pH 7.5; bovine serum components

Conjugate buffer: Tris 25 mM pH 7.5; bovine serum components

Conjugate: peroxidase-(POD) labeled sheep anti-digoxigenin antibodies

Substrate: ABTS® substrate solution (2.2'azino-di[3-ethylbenzthiazoline sulfonate] 1.9 mmol/l in 100 mmol/l phosphate/citrate buffer, pH 4.4, sodium perborate 3.2 mmol/l The following substances are used as receptors R1 to R6 (Bi=abbreviation of biotin, Dig=abbreviation of digoxigenin):

R1: mAb<p24>M-6A9/5-IgG-Bi, mAb<p24>M-4B1/1-IgG-Bi

R2: mAb<p24>M-6D9/4-IgG-Dig, mAb<p24>M-2E7/3-IgG-Dig

R3: gp36-, gp41-peptides-Bi and polyhaptens-Bi according to the peptides used in the Enzymun® test anti-HIV1+2+Sub0, ref. no. 1557319, Boehringer Mannheim Germany R4: gp36-, gp41-peptides-Dig and polyhaptens-Dig according to the peptides used in the Enzymun® test anti-HIV1+2+Sub0, ref. no. 1557319, Boehringer Mannheim Germany R5: RT-Bi produced from RT, ref. no. 1465333, Boehringer Mannheim Germany R6: RT-Dig produced from RT, ref. no. 1465333, Boehringer Mannheim Germany The necessary derivatizations with activated biotin and digoxigenin derivatives were performed according to procedures taken from textbooks and known to the expert. For the derivatization of RT or antibodies the substances preferably used are D-biotin-ε-aminohexanoyl-N-hydroxy-succinimide and digoxigenin-3-carboxymethylether-ε-aminohexanoyl-N-hydroxy-succinimide.

The receptors R1 to R6 (antibodies, polyhaptens and RT 50–300 ng/ml each, peptides 5–50 ng/ml) are transferred to the streptavidin-coated tubes together with the incubation buffer and incubated for 120 minutes. After several washing steps and a 60-minute incubation with the conjugate the substrate solution is added and the extinction values of the resulting dye solutions are determined photometrically at 422 nm after 60 minutes.

Example 2

Comparison of Different Combination Tests

To compare the invention with the state of the art commercially available HIV seroconversion panels from Boston Biomedica Inc., Bridgewater, USA (BBI) were measured and compared to the data delivered by BBI (table 1).

BBI panel N: ref. no. PRB914
BBI panel W: ref. no. PRB923
BBI panel AG: ref. no. PRB932
HIV-Ag test: Abbott Monoclonal HIV Ag, prod. no. 2A81 (BBI data)
Anti-HIV test 1: Abbott HIV½, prod. no. 3A77 (BBI data)
Anti-HIV test 2: Gen. Sys. HIV½, prod. no. 0230 (BBI data)
Combination test 1: Anti-p24 antibody, gp41 and gp36 (description see below)
Combination test 2: Anti-p24 antibody and RT (description see below)
Combination test 3: Anti-p24 antibody, gp41, gp36 and RT (description see below)

The three combination tests were performed under identical conditions with the same reagents except the individual antigens used. The test procedure is analogous to example 1. The basic substances (as in example1) were the reagents and the application of the commercially available Enzymun test® anti-HIV1+2+Subtype0 (ref. no. 1557319, Boehringer Mannheim, Germany) at 25° C. The following antibodies or antigens were used for the combination tests 1 to 3.

Combination Test 1 mAb<p24>M-6A9/5-IgG-Bi, mAb<p24>M-4B1/1-IgG-Bi and biotinylated synthetic peptides and polyhaptens (gp41 and gp36) from the Enzymun test® anti-HIV1+2+Subtype0, mAb<p24>M-6D9/4-IgG-Dig, mAb<p24>M-2E7/3-IgG-Dig and digoxigenylated synthetic peptides and polyhaptens (gp41 and gp36) from the Enzymun test® anti-HIV1+2+Subtype0

Combination Test 2 mAb<p24>M-6A9/5-IgG-Bi, mAb<p24>M-4B1/1-IgG-Bi and biotinylated recombinant HIV reverse transcriptase mAb<p24>M-6D9/4-IgG-Dig, mAb<p24>M-2E7/3-IgG-Dig and digoxigenylated recombinant HIV reverse transcriptase Combination Test 3 (According to the Invention)

R1: mAb<p24>M-6A9/5-IgG-Bi, mAb<p24>M-4B1/1-IgG-Bi,

R3: Biotinylated synthetic peptides and polyhaptens (gp41 and gp36) from the Enzymun test® anti-HIV1+2+Subtype0

R5: Biotinylated recombinant HIV reverse transcriptase

R2: mAb<p24>M-6D9/4-IgG-Dig, mAb<p24>M-2E7/3-IgG-Dig

R4: Digoxigenylated synthetic peptides and polyhaptens (gp41 and gp36) from the Enzymun test® anti-HIV1+2+Subtype0

R6: Digoxigenylated recombinant HIV reverse transcriptase

The signal/cut-off ratio is given for all tests (cut-off index, coi). The data are interpreted as follows: values below 0.9 are negative, values between 0.9 and 1.0 are in the transition region and values $\geq 1.0$ are positive. The column "day" shows the number of days passed since the first blood taking registered. The panels used contain different analytes (antigens and antibodies) occurring in the seroconversion phase after the times indicated under "day".

TABLE 1

Comparison of different HIV detection tests

| Panel | Day | HIV-Ag test | Anti-HIV test 1 | Anti-HIV test 2 | Combi test 1 | Combi test 2 | Combi test 3 |
|---|---|---|---|---|---|---|---|
| BBI panel N | 0 | 0.4 | 8.4 | 0.8 | 8.9 | 0.4 | 11.3 |
| | 4 | 0.5 | 7.8 | 1.1 | 5.7 | 0.1 | 7.4 |
| | 7 | 0.5 | 8.0 | 1.4 | 3.5 | 0.1 | 4.5 |
| | 25 | 0.4 | 12.8 | 2.8 | 1.4 | 0.8 | 3.3 |
| | 31 | 0.4 | 11.4 | 3.0 | 1.1 | 2.3 | 4.3 |
| BBI panel W | 0 | 0.4 | 0.1 | 0.2 | 0.3 | 0.2 | 0.3 |
| | 7 | 0.4 | 0.1 | 0.2 | 0.3 | 0.1 | 0.3 |
| | 12 | 0.5 | 0.1 | 0.2 | 0.3 | 0.1 | 0.3 |
| | 14 | 0.4 | 0.1 | 0.2 | 0.3 | 0.1 | 0.3 |
| | 28 | 0.4 | 0.1 | 0.2 | 0.3 | 0.1 | 0.3 |
| | 30 | 0.4 | 0.1 | 0.2 | 0.3 | 0.1 | 0.3 |
| | 35 | 0.4 | 0.1 | 0.2 | 0.3 | 0.1 | 0.3 |
| | 37 | 1.0 | 0.1 | 0.2 | 0.4 | 0.2 | 0.4 |
| | 47 | 23.3 | 1.4 | 0.2 | 8.4 | 10.9 | 14.3 |
| | 84 | 0.4 | 7.8 | 5.5 | 1.2 | 24.3 | 16.6 |
| | 86 | 0.4 | 7.6 | 5.5 | 1.2 | 24.3 | 16.1 |
| | 145 | 0.4 | 17.2 | 4.0 | 6.5 | 24.3 | 24.8 |
| | 161 | 0.5 | 17.2 | 3.1 | 6.4 | 24.3 | 24.8 |
| BBI panel AG | 0 | 0.4 | 0.1 | 0.1 | 0.3 | 0.2 | 0.3 |
| | 3 | 0.4 | 0.1 | 0.1 | 0.3 | 0.5 | 0.3 |
| | 13 | 0.4 | 0.2 | 0.2 | 0.3 | 0.2 | 0.3 |
| | 27 | 4.6 | 1.1 | 0.2 | 1.1 | 1.0 | 1.1 |
| | 34 | 6.1 | 12.5 | 2.6 | 10.0 | 9.2 | 21.9 |
| | 50 | 1.9 | 1.7 | 3.4 | 4.7 | 24.2 | 14.4 |
| | 78 | 3.2 | 0.6 | 1.3 | 2.3 | 24.3 | 12.7 |
| | 163 | 1.8 | 2.1 | 0.9 | 0.8 | 17.3 | 7.6 |
| | 194 | 1.0 | 8.6 | 0.8 | 0.8 | 13.1 | 6.4 |

It can be seen that in contrast to the comparison tests the combination test according to the invention (combination test 3) detects all phases of infection completely.

Example 3

Recognition of HIV1 Virus Isolates of Different Subtypes

The use of the four antibodies according to the invention ensures a broad HIV1 subtype recognition. The test procedure, reagent composition and evaluation are the same as in the combination test 3 according to the invention of as described in example 2. As samples all HIV1 virus isolates (group M and subtype0) listed below were diluted since all undiluted isolates gave the same maximum signal and showed therefore no difference.

TABLE 2

| HIV1 virus | Subtype | cut-off index |
|---|---|---|
| MP20 | Subtype A | 9.0 |
| MP33 | Subtype A | 22.2 |
| MP95 | Subtype A | 19.2 |
| MP97 | Subtype A | 9.1 |
| MP157 | Subtype A | 36.0 |
| MP8 | Subtype B | 23.4 |
| MP13 | Subtype B | 18.7 |
| MP22 | Subtype B | 22.5 |
| MP51 | Subtype B | 20.9 |
| MP77 | Subtype B | 30.5 |
| MP37 | Subtype C | 9.1 |
| MP40 | Subtype C | 22.2 |
| MP41 | Subtype C | 9.1 |
| MP76 | Subtype C | 18.2 |
| MP148 | Subtype C | 16.4 |
| VI693 | Subtype D | 16.9 |
| VI722 | Subtype D | 10.5 |
| VI824 | Subtype D | 16.3 |

TABLE 2-continued

| HIV1 virus | Subtype | cut-off index |
|---|---|---|
| VI979 | Subtype D | 23.2 |
| VI1091 | Subtype D | 14.9 |
| VI1249 | Subtype E | 23.4 |
| MP38 | Subtype E | 19.4 |
| MP48 | Subtype E | 21.0 |

TABLE 2-continued

| HIV1 virus | Subtype | cut-off index |
|---|---|---|
| MP121 | Subtype E | 22.6 |
| MP126 | Subtype E | 2.5 |
| VI850 | Subtype F | 11.0 |
| VI961 | Subtype F | 22.3 |
| VI1126 | Subtype F | 11.4 |
| VI1267 | Subtype F | 15.3 |
| VI310 | Subtype F | 21.4 |
| MP84 | Subtype F | 12.2 |
| VI1197 | Subtype G | 29.9 |
| VI991 | Subtype H | 8.1 |
| VI997 | Subtype H | 10.0 |
| MP331 | Subtype 0 | 4.2 |

It can be seen that the combination test according to the invention detects the antigens and antibodies of all HIV1 subtypes reliably.

Example 4

Epitope Mapping of the Monoclonal Antibodies Against p24

4.1 Peptide Synthesis

The relevant partial sequences of the amino acid sequence of the HIV-p24 virus protein are produced by means of fluorenyl-methyl-oxycarbonyl-(Fmoc)-solid-phase peptide synthesis on a batch peptide synthesizer, e.g. from Applied Biosystems A431 or A433. For this, 4.0 equivalents each of the following Fmoc amino acid derivatives are used:

TABLE 3

| A | Fmoc-Ala-OH |
|---|---|
| C | Fmoc-Cys(Trt)-OH |
| D | Fmoc-Asp(tBu)-OH |
| E | Fmoc-Glu(tBu)-OH |
| F | Fmoc-Phe-OH |
| G | Fmoc-Gly-OH |
| H | Fmoc-His(Trt)-OH |
| I | Fmoc-Ile-OH |
| K | Fmoc-Lys(Phenylacetyl)-OH |
| L | Fmoc-Leu-OH |
| M | Fmoc-Met-OH |
| N | Fmoc-Asn(Trt)-OH |
| P | Fmoc-Pro-OH |
| Q | Fmoc-Gln(Trt)-OH |
| R | Fmoc-Arg(Pmc)-OH |
| S | Fmoc-Ser(tBu)-OH |
| T | Fmoc-Thr(tBu)-OH |
| U | Fmoc-β alanine |
| V | Fmoc-Val-OH |
| W | Fmoc-Trp-OH |
| X | Boc-Lys(Fmoc)-OH |
| Y | Fmoc-Tyr(tBu)-OH |
| Z | Fmoc-amino-caproic acid |

The amino acids or amino acid derivatives are dissolved in N-methyl pyrrolidone. The peptide is built up on 400 to 500 mg 4-(2',4'-dimethoxyphenyl-Fmoc-aminomethyl)-phenoxy resin (Tetrahedron Letters 28 (1987), 2107) with a loading of 0.4–0.7 mmol/g (JACS 95 (1973), 1328). The coupling reactions for Fmoc-amino-acid derivative are performed during 20 min with 4 dicyclohexylcarbodiimide equivalents and 4 N-hydroxy-benzotriazole equivalents in dimethylformamide as a reaction medium. After each synthesis step the Fmoc group is seperated with 20% piperidine in dimethylformamide within 20 min. If the peptides contain an intramolecular disulfide bridge the Fmoc-protected peptide sequence is oxidized on the solid phase before coupling of the artificial spacer with iodine in hexafluorisopropanol/dichloromethane (Kober et al., The Peptide Academic Press, New York, 1981, pp. 145–47); subsequently the N-terminal Fmoc protective group is separated and the spacer as well as the N-terminal biotin are coupled.

The release of the peptide from the synthetic resin and the cleavage of the acid-labile protective groups—with the exception of the phenylacetyl protective group at the lysine—is carried out with 20 ml of trifluoroacetic acid, 0.5 ml ethanedithiol, 1 ml thioanisol, 1.5 phenol and 1 ml water in 40 min at room temperature. The reaction solution is subsequently mixed with 300 ml cooled diisopropylether and for complete precipitation of the peptide preserved at 0° C. for 40 min. The precipitate is filtrated, washed with diisopropylether, dissolved with a small amount of 50% acetic acid and then lyophilized. The raw material obtained is purified by preparative HPLC on Delta-PAK RP C18 material (column 50×300 mm, 100 Å, 15µ) above a corresponding gradient (eluent A: water, 0.1% trifluoroacetic acid, eluent B: acetrile, 0.1% trifluoroacetic acid) in 120 min. The identity of the material eluted is checked by means of ionic spray mass spectrometry.

TABLE 4

Peptide sequences of the p24 epitopes

| Peptide | Sequence | SEQ ID NO |
|---|---|---|
| 1 | DKGNSSQVSQNYPIVQNLQGQMVHQ | 1 |
| 2 | NYPIVQNLQGQMVHQAISPRTLNAW | 2 |
| 3 | QMVHQAISPRTLNAWVKVIEEKAFS | 3 |
| 4 | TLNAWVKVIEEKAFSPEVIPMFSAL | 4 |
| 5 | EKAFSPEVIPMFSALSEGATPQDLN | 5 |
| 6 | MFSALSEGATPQDLNTMLNTVGGHQ | 6 |
| 7 | PQDLNTMLNTVGGHQAAMQMLKETI | 7 |
| 8 | VGGHQAAMQMLKETINEEAAEWDRV | 8 |
| 9 | LKETINEEAAEWDRVHPVHAGPIAP | 9 |
| 10 | EWDRVHPVHAGPIAPGQMREPRGSD | 10 |
| 11 | GPIAPGQMREPRGSDIAGTTSTLQE | 11 |
| 12 | PRGSDIAGTTSTLQEQIGWMTNNPP | 12 |
| 13 | STLQEQIGWMTNNPPIPVGEIYKRW | 13 |
| 14 | TNNPPIPVGEIYKRWIILGLNKIVR | 14 |
| 15 | IYKRWIILGLNKIVRMYSPVSILDI | 15 |
| 16 | NKIVRMYSPVSILDIRQGPKEPFRD | 16 |
| 17 | SILDIRQGPKEPFRDYVDRFYKTLR | 17 |
| 18 | EPFRDYVDRFYKTLRAEQASQEVKN | 18 |
| 19 | YKTLRAEQASQEVKNWMTETLLVQN | 19 |
| 20 | QEVKNWMTETLLVQNANPDCKTILK | 20 |
| 21 | LLVQNANPDCKTILKALGPAATLEE | 21 |
| 22 | KTILKALGPAATLEEMMTACQGVGG | 22 |
| 23 | ATLEEMMTACQGVGGPGHKARVLAE | 23 |
| 24 | QGVGGPGHKARVLAEAMSQVTNSAT | 24 |
| 25 | RVLAEAMSQVTNSATIMMQRGNFRN | 25 |
| 26 | TNSATIMMQRGNFRNQKKTVKCFNC | 26 |
| 27 | GNFRNQKKTVKCFNCGKEGHIAKNC | 27 |
| 28 | KCFNCGKEGHIAKNCRAPRLKGCWK | 28 |
| 29 | IAKNCRAPRLKGCWKCGKEGHQMKD | 29 |
| 30 | KGCWKCGKEGHQMKDCTERQANFLGKI | 30 |
| 3A | QAISPRTLNAWVKVI | 31 |
| 3B | ISPRTLNAWVK | 32 |
| 9A | INEEAAEWDRVHPVH | 33 |
| 9B | EEAAEWDRVHP | 34 |
| 17A | IRQGPKEPFRDYVDR | 35 |
| 17B | QGPKEPFRDYV | 36 |

4.2. Epitope Mapping 4.2.1. Immunological Testing in General

The characterization of epitopes was performed analogously to the Boehringer Mannheim Enzymun® test anti- HIV1+2 (BM 1 165 062). The test principle follows a 2-step sandwich ELISA with streptavidin technology. But instead of human sera the different monoclonal <p4> antibodies were used and measured with the biotinylated peptides or recombinant p24. The detection is carried out using <mouse IgG>-POD (BM 1 431 323). The remaining additional reagents such as washing solution, streptavidin tubes, ABTS etc. were retained. The measurements were performed on the automatic Enzymun® analytical machines ES 22 or ES 600 from Boehringer Mannheim.

4.2.2. Plateau Determination

The determination of the optimum mAb initial concentration for epitope mapping was carried out in the test conception described above. Biotinylated recombinant p24 (initial quantity of 200 ng/ml) was used as an antigen.

TABLE 5

| | mAb concentration c [µg/ml] | Signal mU |
|---|---|---|
| mAb<p24>-6A9/5 | 0 | 3 |
| | 1 | 208 |
| | 5 | 856 |
| | 10 | 1231 |
| | 20 | 1665 |
| | 25 | 1718 |
| mAb<p24>-6D9/4 | 0 | 2 |
| | 1 | 386 |
| | 5 | 1239 |
| | 10 | 1835 |
| | 20 | 2425 |
| | 25 | 2531 |
| mAb<p24>-2E7/3 | 0 | 5 |
| | 1 | 322 |
| | 5 | 1148 |
| | 10 | 1708 |
| | 20 | 2292 |
| | 25 | 2461 |
| mAb<p24>-4B1/1 | 0 | 9 |
| | 10 | 1205 |
| | 25 | 1944 |
| | 50 | 2116 |
| | 75 | 2451 |
| | 100 | 2537 |

The plateau determination represented graphically in FIGS. 1 to 4.

4.2.3 Epitope Mapping

The mapping carried out with N-terminal biotinylated peptides of 25 amino acids which were synthesized in a pattern of 10 over the HIV1 Consensus B sequence of p24 (peptides with SEQ ID NO: 1–30). First of all a rough mapping with 6 different peptide mixtures A–F (amount used per peptide: 60 ng/ml) containing 5 different biotinylated peptides each were measured with indirect test conception.

| Mixture A: | 1 |
| | 2 |
| | 3 |
| | 4 |
| | 5 |
| Mixture B: | 6 |
| | 7 |
| | 8 |
| | 9 |
| | 10 |
| Mixture C: | 11 |
| | 12 |
| | 13 |
| | 14 |
| | 15 |
| Mixture D: | 16 |
| | 17 |
| | 18 |
| | 19 |
| | 20 |
| Mixture E: | 21 |
| | 22 |
| | 23 |
| | 24 |
| | 25 |
| Mixture F: | 26 |
| | 27 |
| | 28 |
| | 29 |
| | 30 |

TABLE 6

Reactivity of the antibodies with peptide mixtures A–F

| | mAb 6A9/5 | | mAb 4B1/1 | | mAb 6D9/4 | | mAb 2E7/3 | |
|---|---|---|---|---|---|---|---|---|
| | [mU] | % | [mU] | % | [mU] | % | [mU] | % |
| Stnd. antigen | 2098 | 100 | 2402 | 100 | 2966 | 100 | 2903 | 100 |
| Mixture A | 6 | 0 | 29 | 1 | 925 | 31 | 5 | 0 |
| Mixture B | 8 | 0 | 22 | 1 | 100 | 3 | 2696 | 93 |
| Mixture C | 15 | 1 | 31 | 1 | 22 | 1 | 5 | 0 |
| Mixture D | 22 | 1 | 1152 | 48 | 41 | 1 | 4 | 0 |
| Mixture E | 15 | 1 | 17 | 1 | 16 | 1 | 2 | 0 |
| Mixture F | 24 | 1 | 18 | 1 | 17 | 1 | 3 | 0 |

Result of the rough mapping: 3 mAbs react specifically with one peptide mixture each (graphical representation see FIG. 5).

4.2.4. Fine Mapping

For fine mapping the peptides (quantity used: 100 ng/ml) from the reactive mixtures were used separately in the indirect test conception.

TABLE 7 mAB <p24> M-4B1/1 with single antigens from mixture D

| | rec p24 | | peptide 16 | | peptide 17 | | peptide 18 | | peptide 19 | | peptide 20 | |
|---|---|---|---|---|---|---|---|---|---|---|---|---|
| | mU | | mU | | mU | | mU | | mU | | mU | |
| mAb 4B1 | 2089 | 100% | 3 | 0% | 297 | 14% | 2 | 0% | 3 | 0% | 0 | 0% |

TABLE 8 mAb <p24> M-2E7/3 with single antigens from mixture B

| | rec p24 | | peptide 6 | | peptide 7 | | peptide 8 | | peptide 9 | | peptide 10 | |
|---|---|---|---|---|---|---|---|---|---|---|---|---|
| | mU | | mU | | mU | | mU | | mU | | mU | |
| mAb 2E7 | 2111 | 100% | 6 | 0% | 3 | 0% | 23 | 1% | 2103 | 99.6% | 5 | 0% |

TABLE 9 mAb <p24> M-6D9/4 with single antigens from mixture A

| | rec p24 | | peptide 1 | | peptide 2 | | peptide 3 | | peptide 4 | | peptide 5 | |
|---|---|---|---|---|---|---|---|---|---|---|---|---|
| | mU | | mU | | mU | | mU | | mU | | mU | |
| mAb 6D9 | 2282 | 100% | 3 | 0% | 23 | 1% | 922 | 40% | 5 | 0% | 4 | 0% |

TABLE 10

Reactive peptide sequences:

| Peptide SEQ ID NO | Sequence | Result |
|---|---|---|
| 3 | QMVHQAISPRTLNAWVKVIEEKAFS | reactive with mAb<p24>M-6D9 |
| 9 | LKETINEEAAEWDRVHPVHAGPIAP | reactive with mAb<p24>M-2E7/3 |
| 17 | SILDIRQGPKEPFRDYVDRFYKTLR | reactive with mAb<p24>M-4B1/1 |

TABLE 11

Sequence comparison of the epitopes of p24 HIV I Consensus B and subtype 0

| | | |
|---|---|---|
| mAb 6D9 | QMVHQAISPRTLNAWVKVIEEKAFS | Consensus B |
| | QMVHQAISPRTLNAWVKAIEEKAFN | Subtype 0 |
| mAb 2E7 | LKETINEEAAEWDRVHPVHAGPIAP | Consensus B |
| | LKEVINEEA?EWDRTHPP??GPLPP | Subtype 0 |
| mAb 4B1 | SILDIRQGPKEPFRDYVDRFYKTLR | Consensus B |
| | SILDI?QGPKEPFRDYVDRFYKTLR | Subtype 0 |

According to the sequence comparison the mAbs 6D9 and 4B1 should allow the cross reaction with p24 (Sub0) since there is the most extensive homology in the sequence.

For further confinement of the epitope a second fine mapping was performed with the peptides 3 (=SEQ ID NO 3), 3A (=SEQ ID NO 31), 3B (=SEQ ID NO 32) and mAb<p24>M-6D9/4; peptide 9 (SEQ ID NO 9), 9A (=SEQ ID NO 33), 9B (=SEQ ID NO 34) and mAb<p24>M-2E7/3; as well as peptide 17 (=SEQ ID NO 17), 17A (=SEQ ID NO 35), 17B (=SEQ ID NO 36) and mAb<p24>M-4B1/1.

TABLE 12 mAb<p24>M-4B1/1 with single antigens 17, 17A and 17B

| | Peptide 17 | Peptide 17A | Peptide 17B |
|---|---|---|---|
| SEQ ID NO | 17 | 35 | 36 |
| | mU | mU | mU |
| mAb 4B1/1 | 612 | 10 | 7 |

TABLE 13 mAb<p24>M-2E7/3 with single antigens 9, 9A and 9B

| | Peptide 9 | Peptide 9A | Peptide 9B |
|---|---|---|---|
| SEQ ID NO | 9 | 33 | 34 |
| | mU | mU | mU |
| mAb 2E7/3 | 1439 | 1330 | 1399 |

TABLE 14 mAb<p24>M-6D9/4 with single antigens 3, 3A and 3B

| | Peptide 3 | Peptide 3A | Peptide 3B |
|---|---|---|---|
| SEQ ID NO | 3 | 31 | 32 |
| | mU | mU | mU |
| mAb 6D9/4 | 958 | 866 | 448 |

It follows from this that the epitope of the antibody mAb<p24>M-4B1/1 cannot be confined mAb<p24>M-2E7/3 can be minimized to the following sequence:

9B (SEQ ID NO: 34) EEAAEWDRVHP

The epitope of the mAb<p24>M-6D9/4 can be shortened—without important signal loss—to the following sequence:

3A (SEQ ID NO: 31) QAISPRTLNAWVKVI

Example 5
HIV Subtype Recognition by Monoclonal anti-p24 Antibodies

The test was carried out according to example 1 and 2 following the principles of the Enzymun test® anti-HIV1+2+Subtype0 (ref. no. 1557319, Boehringer Mannheim, Germany). For testing the HIV subtype recognition, however, only the receptors R1 and R2, i.e. the monoclonal antibodies against p24 were used. The amount used was 250 ng mAb/ml each.

TABLE 15

Recognition of p24 (HIV1 and HIV1-Sub0) by mAbs

| | Receptor R1 | | | | |
|---|---|---|---|---|---|
| | mAb 4B1/1 | mAb 2E7/3 | mAb 4B1/1 | mAb 6A9 | mAb 4B1/1 mAb 6A9/5 |
| | | | Receptor R2 | | |
| Sample | mAb 2E7/3 | mAb 6D9/4 | mAb 6D9/4 | mAb 6D9/4 | mAb 2E7/3 mAb 6D9/4 |
| SN 1806 (HIV1 subtype 0) | 0.1 (negative) | 0.1 (negative) | 1.2 (positive) | 0.1 (negative) | 1.2 (positive) |
| SN 1807 (HIV1 subtype 0) | 0.1 (negative) | 0.1 (negative) | 1.7 (positive) | 0.1 (negative) | 1.7 (positive) |
| SN 1796 (HIV1) | 1.1 (positive) | 0.1 (negative) | 0.1 (negative) | 0.6 (negative) | 1.2 (positive) |
| SN 1799 (HIV1) | 0.9 (limit) | 1.3 (positive) | 1.2 (positive) | 1.1 (positive) | 1.4 (positive) |
| SN 1801 (HIV1) | 0.8 (limit) | 1.7 (positive) | 0.8 (limit) | 1.3 (positive) | 1.7 (positive) |
| SN 1803 (HIV1) | 1.7 (positive) | 2.2 (positive) | 0.1 (negative) | 0.5 (negative) | 2.3 (positive) |

It is shown that the monoclonal antibody mAb<p24>M-4B1/1 and the monoclonal antibody mAb<p24>M-6A9/5 are each suitable for use as R1, i.e. on the side of the solid phase. The monoclonal antibodies mAb<p24>M-6D9/4 and mAb<p24>M-6D9/4 are preferably suitable for use as R2, i.e. on the detection side. For an efficient simultaneous recognition of the p24 of HIV1 and HIV1-Sub0 all four antibodies are preferably used together.

What is claimed is:

1. An immunoassay method for the detection of at least one of antibodies and antigens of each of HIV1, HIV1-sub0 and HIV2 in a sample suspected of containing said antibodies and antigens, the method comprising:

a) incubating binding partners R1 and R2 in a sample mixture comprising at least a portion of said sample,
        wherein R1 binds specifically to an antigen selected from the group consisting of the p24 antigen of HIV1, the p24 antigen of HIV1-Sub0 and the p26 antigen of HIV2, R1 being bound directly or indirectly to a first solid phase, and
        wherein R2 binds specifically to said antigen, R2 being bound to a first detectable label, and R2 recognizing an epitope different from that recognized by R1, whereby the antigen forms a sandwich with R1 and R2;
    b) incubating binding partners R3 and R4 in a sample mixture comprising at least a portion of said sample,
        wherein R3 binds specifically to a first antibody selected from the group consisting of antibodies against an antigen of the env region HIV1, HIV1-Sub0 and HIV2, R3 being bound directly or indirectly to a second solid phase, and
        wherein R4 binds specifically to the first antibody, R4 being bound to a second detectable label, whereby said first antibody forms a bridge between R3 and R4;
    c) incubating binding partners R5 and R6 in a sample mixture comprising at least a portion of said sample,
        wherein R5 binds specifically to a second antibody selected from the group consisting of antibodies against an antigen of the pol and gag regions of HIV1, HIV-Sub0 and HIV2, wherein the gag regions exclude sequences of p24 and p26, R5 being bound directly or indirectly to a third solid phase, and
        wherein R6 binds specifically to the second antibody, R6 being bound to a third detectable label, whereby the second antibody forms a bridge between R5 and R6; and
    d) determining the amount of the detectable labels bound to the solid phases or remaining unbound as a measure of the antibodies and the antigens of HIV1, HIV1-sub0, and HIV2 in the sample;

wherein at least one of R1, R3, and R5 binds specifically to at least one of antibodies and antigens of HIV1; at least one of R1, R3, and R5 binds specifically to at least one of antibodies and antigens of HIV-Sub0; and at least one of R1, R3, and R5 binds specifically to at least one of antibodies and antigens of HIV2.

2. The method of claim 1, wherein R1 is an antibody produced from a cell line selected from the group consisting of cell lines mAb<p24>M-6A9/5, deposit number DSM ACC2310, mAb<p24>M-4B1/1, deposit number DSM ACC2299, mAb<p24>M-6D9/4, deposit number DSM ACC2300 or mAb<p24>M-2E7/3, deposit number DSM ACC2301.

3. The method of claim 1, wherein R1 is an antibody against an HIV1 p24 antigen, the antibody binding in an equivalent way to an antibody produced from a cell line selected from the group consisting of cell lines mAb<p24>M-6A9/5, deposit number DSM ACC2310, mAb<p24>M-4B1/1, deposit number DSM ACC2299, mAb<p24>M-6D9/4, deposit number DSM ACC2300 or mAb<p24>M-2E7/3, deposit number DSM ACC2301.

4. The method of claim 1, wherein R1 is an antibody against an HIV1 p24 antigen, the antibody binding to the same epitope as an antibody produced from a cell line selected from the group consisting of cell lines mAb<p24>M-6A9/5, deposit number DSM ACC2310, mAb<p24>M-4B1/1, deposit number DSM ACC2299, mAb<p24>M-6D9/4, deposit number DSM ACC2300 or mAb<p24>M-2E7/3, deposit number DSM ACC2301.

5. The method of claim 1, wherein the incubating binding partners R1 and R2 and the incubating binding partners R3 and R4 are performed simultaneously in the same sample mixture.

6. The method of claim 1, wherein the incubating binding partners R3 and R4 and the incubating binding partners R5 and R6 are performed simultaneously in the same sample mixture.

7. The method of claim 1, wherein the incubating binding partners R1 and R2 and the incubating binding partners R5 and R6 are performed simultaneously in the same sample mixture.

8. The method of claim 1, wherein the incubating binding partners R1 and R2, the incubating binding partners R3 and R4, and the incubating binding partners R5 and R6 are performed simultaneously in the same sample mixture.

9. The method of claim 1, wherein the sample is selected from a group consisting of whole blood, blood sera, blood plasma, urine, and saliva.

10. A reagent kit for detection of an HIV infection, said kit comprising:

binding partners R1, R2, R3, R4, R5, and R6;

wherein R1 binds specifically to an antigen selected from the group consisting of the p24 antigen of HIV1, the p24 antigen of HIV1-Sub0 and the p26 antigen of HIV2, R1 being bound directly or indirectly to a solid phase;

R2 binds specifically to said antigen, R2 being bound to a detectable label, and R2 recognizing an epitope different from that recognized by R1, whereby said antigen forms a sandwich with R1 and R2;

R3 binds specifically to a first antibody selected from the group consisting of antibodies against an antigen of the env region of HIV1, HIV1-Sub0 and HIV2, R3 being bound directly or indirectly to a solid phase;

R4 binds specifically to said first antibody, R4 being bound to a detectable label, whereby said first antibody forms a bridge between R3 and R4;

R5 binds specifically to a second antibody selected from the group consisting of antibodies against an antigen of the pol and gag regions of HIV1, HIV1-Sub-0 and HIV2, wherein said gag regions exclude sequences of p24 and p26, R5 being bound directly or indirectly to a solid phase;

R6 binds specifically to said second antibody, R6 being bound to a detectable label, whereby said second antibody forms a bridge between R5 and R6; and wherein at least one of R1, R3, and R5 binds specifically to at least one of antibodies and antigens of HIV1; at least one of R1, R3, and R5 binds specifically to at least one of antibodies and antigens of HIV-Sub0; and at least one of R1, R3, and R5 binds specifically to at least one of antibodies and antigens of HIV2.

11. The reagent kit of claim 10, wherein R1 comprises an antibody produced from a cell line selected from the group consisting of cell lines mAb<p24>M-6A9/5, deposit number DSM ACC2310, mAb<p24>M-4B1/1, deposit number DSM ACC2299, mAb<p24>M-6D9/4, deposit number DSM ACC2300 or mAb<p24>M-2E7/3, deposit number DSM ACC2301.

12. The reagent kit of claim 10, wherein R2 comprises an antibody produced from a cell line selected from the group consisting of cell lines mAb<p24>M-6A9/5, deposit number DSM ACC2310, mAb<p24>M-4B1/1, deposit number DSM ACC2299, mAb<p24>M-6D9/4, deposit number DSM ACC2300 or mAb<p24>M-2E7/3, deposit number DSM ACC2301.

* * * * *